United States Patent [19]

Kiikka et al.

[11] 4,291,181

[45] Sep. 22, 1981

[54] INDENES FROM TETRAHYDROINDENES

[75] Inventors: Oliver A. Kiikka, Willoughby; George S. Li, Macedonia, both of Ohio

[73] Assignee: Standard Oil Company, Cleveland, Ohio

[21] Appl. No.: 108,258

[22] Filed: Dec. 28, 1979

[51] Int. Cl.[3] .................. C07C 5/42; C07C 5/367; C07C 4/12; C07C 5/48

[52] U.S. Cl. ............................ 585/320; 585/361; 585/400; 585/410; 585/415; 585/422; 585/430; 585/431; 585/433; 585/443; 585/444

[58] Field of Search ............ 585/27, 319, 320, 361, 585/400, 410, 415, 422, 430, 431, 433, 443, 444

[56] References Cited

U.S. PATENT DOCUMENTS

| | | | |
|---|---|---|---|
| 2,519,577 | 8/1950 | Ipatieff | 585/410 |
| 2,763,701 | 9/1956 | Hoffmann et al. | 585/400 |
| 2,984,692 | 5/1961 | Lederle | 585/400 |
| 3,183,249 | 5/1965 | Weise | 585/360 |
| 3,502,736 | 3/1970 | Sato et al. | 585/443 |
| 3,728,406 | 4/1973 | Vrinssen et al. | 585/360 |
| 3,853,291 | 12/1974 | Feins | 208/216 PP |
| 3,887,631 | 6/1975 | Yaffe | 585/445 |
| 3,925,498 | 12/1975 | Stadig | 585/625 |
| 3,933,932 | 1/1976 | Vrieland et al. | 585/444 |
| 4,143,082 | 3/1979 | Bartek et al. | 585/437 |

*Primary Examiner*—Curtis R. Davis
*Attorney, Agent, or Firm*—John E. Miller, Jr.; Herbert D. Knudsen; Larry W. Evans

[57] ABSTRACT

A dehydrogenation process for producing indene and substituted indenes from tetrahydroindene or substituted tetrahydroindene is described and comprises contacting said tetrahydroindene or substituted tetrahydroindene with a catalyst comprising cobalt oxide and molybdenum oxide at an elevated temperature for a period of from about 0.1 to 30 seconds. The tetrahydroindene and substituted tetrahydroindenes may be prepared from cyclopentadiene or dicyclopentadiene and a butadiene.

15 Claims, No Drawings

INDENES FROM TETRAHYDROINDENES

BACKGROUND OF THE INVENTION

This invention relates to an improved dehydrogenation process for producing indene and substituted indenes, and more particularly, to a dehydrogenation process utilizing a composite catalyst comprising cobalt oxide and molybdenum oxide. Indene is present in low concentrations (e.g. 12–16%) in ethylene or gas oil cracking coproducts, but it has been difficult to recover the indene in satisfactory yields and purity from these low concentration sources. Indene is a desirable raw material for preparing superior heat-resistant polymers.

The invention of this application is directed particularly to the preparation of indene and substituted indene from tetrahydroindene and substituted tetrahydroindene. Tetrahydroindene along with other products are formed in Diels-Alder reactions of butadiene with cyclopentadiene or its dimer, dicyclopentadiene. Substituted tetrahydroindenes are obtained when a substituted butadiene is used in the reaction. A considerable amount of research has been conducted and published on this reaction, and various suggestions have been made for optimizing the production of the various coproducts such as vinyl cyclohexane and vinyl norbornene. Attempts to separate the coproducts, and particularly, the tetrahydroindene, generally have been unsuccessful.

U.S. Pat. No. 3,183,249 describes the preparation of 5-vinyl norbornene-2 by the thermal Diels-Alder type reaction of butadiene and cyclopentadiene at a temperature of 100°–400° C. at pressures of from 2 to 75 atmospheres and a reaction time of 1–3 hours. The process of the patent results in conversion efficiencies to 5-vinyl norbornene-2 of about 20%. The remainder of the converted cyclopentadiene is converted into a large variety of undesirable byproducts. In U.S. Pat. No. 3,728,406, 5-vinyl norbornene-2 is prepared by reacting cyclopentadiene and/or dicyclopentadiene with butadiene, the reaction being discontinued when no more than 50% of the cyclopentadiene has been converted whereby the efficiency of converted raw material into vinyl norbornene is improved.

The dehydrogenation of indene precursers such as tetrahydroindene into indene has been described in the art and generally is conducted in the presence of dehydrogenation promoting catalysts. In U.S. Pat. No. 4,143,082, the dehydrogenation of indene precursers into indene is accomplished by contacting the indene precurser in the presence of an oxygen donor with a phosphate catalyst at elevated temperature. These catalysts, described more fully in the patent, are salts of one of the phosphoric acids. Other types of dehydrogenation catalyst have been described in the literature, and such compounds include the metal oxides, metal salts such as the halides, phosphates, sulfates, molybdates, tungstates, etc. Generally, these catalysts are characterized as compounds containing a metal having a polyoxidation state, that is, a metal having at least two oxidation states in addition to the zero state. Examples of useful polyoxidation state metals include Ti, V, Cr, Mn, Co, Ni, Cu, Nb, Mo, Ru, etc.

In addition to the use of polyoxidative state metals, oxidation catalysts also may be combined with one or more monooxidation state metals which act as promoters, initiators, stabilizers and the like. The single oxidation state metal or metal compounds include the alkali metals, and polyvalent metals such as magnesium, aluminum, calcium, scandium, zinc, etc. The use of cobalt and molybdenum oxides promoted with potassium oxide in dehydrogenating indane to indene is reported in Czech Patent No. 135,251. The catalyst bed contained 3% CoO, 10% $MoO_3$ and 0.3% $K_2O$. A review of the various catalysts useful in oxidative dehydrogenation of organic compounds is found in U.S. Pat. No. 3,925,498.

SUMMARY OF THE INVENTION

It now has been found that the highly desirable conversion of tetrahydroindene and substituted tetrahydroindene to indene and indene derivatives can be accomplished at desirable selectivity by a method which comprises contacting said tetrahydroindene or substituted tetrahydroindene with a composite catalyst comprising cobalt oxide and molybdenum oxide at an elevated temperature. Generally, the reactants will be contacted with the catalyst at temperatures of from about 300°–650° C. for a period of from about 0.1 to 30 seconds, preferably from about 0.1 to 10 seconds.

DESCRIPTION OF THE PREFERRED EMBODIMENTS

In accordance with the present invention, indene and substituted indenes are produced from tetrahydroindene and substituted tetrahydroindenes by dehydrogenation utilizing a composite catalyst which comprises cobalt oxide and molybdenum oxide. The invention also relates to the preparation of indene and substituted indenes from tetrahydroindene and substituted tetrahydroindene prepared from the Diels-Alder reaction of cyclopentadiene or dicyclopentadiene with a butadiene. Vinyl norbornene formed in the Diels-Alder reaction is converted to additional tetrahydroindene in a heated tube.

The substituted tetrahydroindenes which can be converted to substituted indenes in accordance with the method of the invention may contain one or more alkyl or alkenyl groups having from one to four carbon atoms attached to one or both rings. The substituted indenes produced from these precursers normally have the corresponding alkyl or alkenyl group attached, although they may have fewer groups or may have groups with fewer carbon atoms attached.

In carrying out the process of the invention, the tetrahydroindene or substituted tetrahydroindene is contacted with a composite catalyst which comprises cobalt oxide and molybdenum oxide at an elevated temperature for a period of from about 0.1 to 30 seconds. The useful cobalt-molybdenum catalysts are commercially available from a variety of sources including the Nalco Chemical Company, Houston, Texas, and American Cyanamid Company, Bound Brook, New Jersey. These catalysts generally are contained on a support material such as carbon or alumina. U.S. Pat. No. 3,853,791 describes a variety of methods for preparing cobalt-molybdenum oxide catalysts on an alumina support.

The catalysts which are useful in the present invention generally contain from about 1–8% cobalt and from about 8–20% of molybdenum, the percentages being by weight based on the weight of the composite and expressed as the metal oxides. The term alumina support as used in the art and in this application describes substantially pure alumina or alumina containing minor amounts, for example up to about ten weight percent, of known stabilizers such as silica. The chemical analysis of a typical commercially available cobalt-molybdenum catalyst (Nalco Sphericat 477) is as follows: $MoO_3$, 12.5%; CoO, 3.5%; $Na_2O$, 0.08%; Fe, 0.03%; $SiO_2$, 1.5%; and $Al_2O_3$, balance.

The tetrahydroindene or substituted tetrahydroindene is contacted in the vapor state with the catalyst at an elevated temperature generally from about 300° to about 650° C. and preferably from about 500° to about 650° C. The contact time can range from about 0.1 to about 30 seconds although shorter contact periods of from about 0.1 to 10 seconds are preferred. If the contact time is too long, back hydrogenation of the indene to tetrahydro and hexahydroindene is possible.

In one preferred embodiment, dehydrogenation of tetrahydroindene is conducted over the cobalt-molybdenum catalyst and steam at 0.9 lb/lb tetrahydroindene. The conversion of tetrahydroindene is 99.6% at a temperature of 515° C. and about one second contact time.

Although the cobalt-molybdenum catalysts described above are useful in the dehydrogenation reactions of the invention, it has been found that improved results are obtained when the promoters for the catalysts are included. It appears that the presence of the promoter reduces the extent of catalyst fouling caused at least in part by the formation of carbon deposits on the catalyst during the dehydrogenation reaction.

Alkaline metal compounds can be included with the catalyst in limited quantities as a promoter for the catalytic reaction. Examples of particularly useful promoters include potassium oxide, cesium oxide and rubidium oxide. Although the optimum type and quantity of promoter may vary depending upon the reaction conditions and the reactants, the use of potassium oxide in quantities of up to 2% or more generally is preferred.

The efficacy of the method of the invention for producing indene and substituted indenes from tetrahydroindene and substituted indenes is illustrated in the following examples which are conducted on tetrahydroindene in a 20 cc. fixed bed reactor. The general procedure is as follows. Nitrogen is bubbled through a saturator containing the indene precurser and water and this mixed feed enters the reactor. The rates, including product of gas, are measured by timing bubble travel in a 50 cc. burette. The feed rate is determined by weighing the saturator before and after a series of runs knowing the on-stream time. The residual feed is split into a hydrocarbon-water fraction to determine the actual amounts of each feed.

The reactor effluent is collected in two knock-out flasks connected in series and mounted in an ice bath. The second flask contains distilled water. Most of the liquid product recovered generally is condensed in the first flask (90+%). This product is analyzed by gas chromatography and no solvents or dilution is used. The retention times are confirmed either by spiking the liquid product or running separately high purity knowns.

The catalyst used in Examples 1 and 2 (untreated) is available commercially under the general trade designation "Aero HDS-Catalyst" from American Cyanamid, Bound Brook, New Jersey. This catalyst analyzes 12.8% $MoO_3$, 6.0% CoO, 0.03% $Na_2O$ and 0.03% Fe. The catalyst used in the following examples 3-5 is Nalcomo 477, an extruded cobalt molybdenum catalyst available from Nalco Chemical Company analyzing, on a dry basis, 12.5% $MoO_3$, 3.5% CoO, 0.08% $Na_2O$, 0.03% Fe, 1.5% $SiO_2$ and the balance $Al_2O_3$.

| Example[1] | Catalyst | Temp (C.°) | Contact Time (sec) | Conversion (%) | Indene (%) | Indane (%) | Indene Selectivity (%) | Total Selectivity (%) |
|---|---|---|---|---|---|---|---|---|
| 1 | HDS-10[2] | 460 | 1.08 | 90.6 | 23.14 | 61.28 | 27 | 93 |
| 2 | HDS-10[2] | 515 | 1.01 | 99.6 | 54.30 | 39.70 | 57.9 | 94 |
| 3 | Nalcomo-477 | 460 | 0.34 | 89.4 | 23.30 | 59.97 | 27.5 | 93 |
| 4 | Nalcomo-477 | 515 | 0.31 | 94.5 | 38.16 | 50.94 | 42.8 | 94 |
| 5 | Nalcomo-477 | 460[3] | 1.12 | 99.6 | 52.86 | 42.10 | 56.3 | 95 |

[1] Water at 0.9 lb/lb is used.
[2] Catalyst treated with $KNO_3$ to give 0.4% $K_2O$, dried and calcined. This at 425° C.
[3] Recorded temperature may be in error The results of the Examples summarized in the table indicate that indene can be prepared by dehydrogenation of tetrahydroindene in a high conversion and desirable indene/indane ratio. Although not reported in the table, the results from the experiments indicated that the non-promoted catalysts had significantly greater carbon deposits than the $K_2O$ promoted catalyst. Specifically, 0.5 grams of carbon is deposited on the catalyst (13.2 gms) in Example 2 whereas 1.5 of carbon is deposited on the catalyst (11.1 gms) in Example 5, an increase of 250% in carbon deposit.

The tetrahydroindene and substituted tetrahydroindenes which are dehydrogenated in accordance with the above described procedure can be obtained from a variety of sources. As mentioned above, the Diels-Alder reaction of dicyclopentadiene or cyclopentadiene with a butadiene results in the formation not only of tetrahydroindene but also in the formation of other products such as vinyl cyclohexane and vinyl-norbornene. In one embodiment of the invention of this application, the Diels-Alder reaction conditions are selected to provide the maximum production of tetrahydroindene which subsequently is converted to indene by dehydrogenation over the composite cobalt-molybdenum catalyst described above. In this embodiment, the tetrahydroindene and vinyl-norbornene are separated from the vinyl cyclohexane, and the vinyl-norbornene is converted (isomerized) to tetrahydroindene in a heated tube. The tetrahydroindene prepared in this manner is combined with the tetrahydroindene formed directly from the Diels-Alder reaction, and this combined product can then be dehydrogenated in accordance with the invention to form indene or substituted indenes in high yields.

Substituted tetrahydroindenes are obtained when a butadiene derivative is reacted with cyclopentadiene or dicyclopentadiene. The butadienes can be represented by the formula

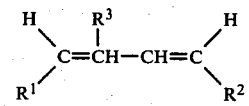

wherein $R^1$, $R^2$ and $R^3$ are each independently hydrogen or a lower alkyl group containing up to four carbon atoms such as methyl, ethyl, n-propyl, etc. $R^3$ also may be a halogen group. Examples of substituted butadienes include isoprene, chloroprene, 1,3-pentadiene, 2,4-hexadiene, 1,3-hexadiene, etc.

The reaction between the cyclopentadiene or dicyclopentadiene and the butadiene or substituted butadiene is conducted at a temperature of 100°–400° C. at pressures corresponding to the total pressure exerted by the reaction compounds. One preferred reaction for preparing tetrahydroindene involves reacting butadiene with dicyclopentadiene in a mole ratio of 2.23:1 at about 210° C. and 600 psig for 75 minutes. The yield of tetrahydroindene from this reaction is increased by isomerizing the vinylnorbornene formed as a coproduct of the Diels-Alder reaction to tetrahydroindene in a hot tube at about 300° C. Polymerization inhibitors can be included in the reaction mixture to reduce formation of heavy or polymeric byproducts. One example of a polymerization inhibitor is N-nitroso-diphenylamine.

The conditions under which the Diels-Alder reaction is conducted should be selected to favor the formation of tetrahydroindene as the major product. For example, it has been reported in Chemical Abstracts, Volume 53:4232d (1959) that higher yields of tetrahydroindene can be obtained if the Diels-Alder reaction is conducted at higher temperature (e.g. 190° C.) and for a longer period of time such as 90 minutes. However, polymer formation also increases as a result of the higher temperature. It is suggested that the higher yield of tetrahydroindene results from the isomerization of vinylnorbornene.

In U.S. Pat. No. 3,183,249 issued to Esso Research, it is suggested that where tetrahydroindene is the desired product, the mole ratio of dicyclopentadiene:butadiene should be in the range of 2–10 and the temperature should be between 200°–300° C. Lower temperatures, e.g., 150°–200° C. favor the formation of vinyl-norbornene.

It is preferred that the vinyl-norbornene formed as a coproduct in the Diels-Alder reaction be isomerized to tetrahydroindene and the tetrahydroindene subsequently dehydrogenated to indene. This procedure is preferred even though vinyl-norbornene can be dehydrogenated to tetrahydroindene because it generally is found that attempts to dehydrogenate vinyl-norbornene results in the formation of the desired indene in poor yields and in the formation of significant amounts of coke substances which rapidly foul most catalysts.

The dehydrogenation process of this invention, using commercially available cobalt-molybdenum catalysts, results generally in the conversion of dihydroindene of 95–100%, particularly at temperatures over 500° C. and with 1 second contact time. The product contains as much as 53% indene and 39% indane indicating a total selectivity of about 92%.

We claim:

1. A dehydrogenation process for producing indene and substituted indenes from tetrahydroindene or substituted tetrahydroindene which comprises contacting said tetrahydroindene or substituted tetrahydroindene with a catalyst comprising cobalt oxide and molybdenum oxide at an elevated temperature for a period of from 0.1 to 30 seconds.

2. The process of claim 1 wherein the substituted tetrahydroindene contains from about 1 to 4 carbon atoms in the substituent.

3. The process of claim 1 wherein the catalyst is treated with a potassium salt solution, dried and calcined prior to use in the process.

4. The process of claim 1 wherein the catalyst comprises from about 8–20% of molybdenum oxide and from about 1–8% of cobalt oxide on a support.

5. The process of claim 1 wherein the temperature is from about 300° to about 650° C.

6. The process of claim 5 wherein the temperature is from about 500° to about 650° C. and the contact time is from 0.1 to 10 seconds.

7. A process for producing indene and substituted indenes which comprises the steps of
    (a) reacting cyclopentadiene or dicyclopentadiene with a butadiene to form a mixture of a tetrahydroindene, vinyl norbornene and vinyl cyclohexene,
    (b) recovering the tetrahydroindene and vinyl norbornene from the mixture,
    (c) converting the vinyl norbornene to a tetrahydroindene in a heated tube and combining said tetrahydroindene with the tetrahydroindene recovered in step (b), and
    (d) dehydrogenating the tetrahydroindene to an indene by contacting said tetrahydroindene with a catalyst comprising molybdenum oxide and cobalt oxide at an elevated temperature for a period of from about 0.1 to 30 seconds.

8. The process of claim 7 wherein the tetrahydroindene is a substituted tetrahydroindene, and the indene recovered from the process is a substituted indene.

9. The process of claim 7 wherein the catalyst comprises from about 8–20% of molybdenum oxide and from about 1–8% of cobalt oxide on a support.

10. The process of claim 7 wherein the catalyst is treated with a potassium salt solution, dried and calcined prior to use in the process.

11. The process of claim 7 wherein the butadiene is reacted with dicyclopentadiene.

12. The process of claim 7 wherein the butadiene is butadiene, isoprene or chloroprene.

13. The process of claim 9 wherein the catalyst comprises from about 8–20% of molybdenum oxide, from about 1–8% of cobalt oxide and from about 1–2% of silica supported on alumina.

14. The process of claim 7 wherein the temperature is from about 500° to 650° C. and the contact with the catalyst is for a period of about 0.1 to 10 seconds.

15. The method of claim 7 wherein the dehydrogenation is promoted with potassium, cesium, or rubidium oxide.

* * * * *